United States Patent [19]

Rohrmann et al.

[11] Patent Number: 4,985,576

[45] Date of Patent: Jan. 15, 1991

[54] BISINDENYL DERIVATIVE, AND A PROCESS FOR THE PREPARATION THEREOF

[75] Inventors: Jürgen Rohrmann, Liederbach; Martin Antberg, Hofheim am Taunus, both of Fed. Rep. of Germany

[73] Assignee: Hoechst Aktiengesellschaft, Frankfurt, Fed. Rep. of Germany

[21] Appl. No.: 458,346

[22] Filed: Dec. 29, 1989

[30] Foreign Application Priority Data

Dec. 30, 1988 [DE] Fed. Rep. of Germany ....... 3844282

[51] Int. Cl.$^5$ .......................... C07F 7/08; C07F 7/18; C07F 7/30
[52] U.S. Cl. ....................... 556/435; 556/9; 556/10; 556/11; 556/12; 556/88; 556/89; 556/95; 556/108; 556/431; 556/432; 556/433; 556/434; 556/453; 556/454; 556/455; 556/457; 556/465; 556/482; 556/485; 556/486; 556/488; 556/489
[58] Field of Search .............. 556/435, 95, 432, 431, 556/432, 434, 453, 454, 455, 457, 88, 89, 108, 9, 10, 11, 12, 465, 482, 485, 486, 488, 489

[56] References Cited

U.S. PATENT DOCUMENTS

| | | | |
|---|---|---|---|
| 3,139,448 | 6/1969 | Hardy et al. | 556/435 |
| 4,501,702 | 2/1985 | Bulten et al. | 556/95 X |
| 4,778,908 | 10/1988 | Pillot et al. | 556/435 |

FOREIGN PATENT DOCUMENTS 0129368 12/1984 European Pat. Off. .............. 556/95

OTHER PUBLICATIONS

Sommer, L.H. et al., *J.A.C.S.* 73:5135-5138 (1951).

*Primary Examiner*—Paul F. Shaver

[57] ABSTRACT

A bisindenyl derivate of the formula I

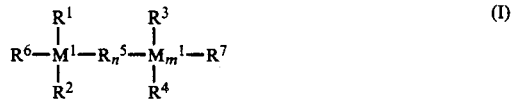

($M^1$ = Si or Ge, $R^6$ and $R^7$ = unsubstituted or substituted idenyl radical)

is obtained in very good yield by reacting a compound of the formula II

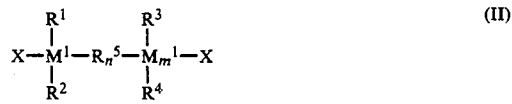

(X = halogen) with a compound of the formula III or IV

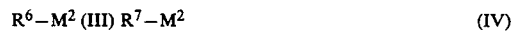

($M^2$ = alkali metal)

if, in the reaction, compound III or IV is added slowly to compound II.

Compound I is suitable as a starting material for the preparation of metallocene catalyst components.

12 Claims, No Drawings

BISINDENYL DERIVATIVE, AND A PROCESS FOR THE PREPARATION THEREOF

DESCRIPTION

Bisindenyl derivative, and a process for the preparation thereof

The present invention relates to an improved process for the preparation of silyl- or germyl-bridged bisindenyl derivatives.

Compounds of this type can be used as ligand systems for constructing chiral, stereorigid metallocene complexes. The zirconium and hafnium dichloride complexes, in particular, can be applied as highly active, stereospecific catalysts for the preparation of highly isotactic polypropylene (cf. EP 129,368).

There is interest in using compounds of the type 1,1'-(R,R'(Si,Ge)bisindenyl (R and R'=alkyl or aryl) for the synthesis of bridged metallocenes, in particular zirconium and hafnium dichloride derivatives.

In the literature, only the synthesis of 1,1'-(dimethylsilanediyl)bisindenyl in a yield of 24% by reacting indenyllithium with dimethyldichlorosilane in xylene has hitherto been described (cf. C. H. Sommer, N. S. Marans, JACS 73 (1951) 5135). In this synthesis, the silyl component was added dropwise to the indenyllithium solution, and the batch was subsequently stirred at 100° C. for 24 hours.

It has now been found that silyl- and germyl-bridged compounds are obtained in substantially high yields and under milder conditions if the sequence of addition is reversed, i.e. the indenyl component is added slowly as a solution to the dichlorosilyl or dichlorogermyl compound.

The invention thus relates to a bisindenyl derivative of the formula I

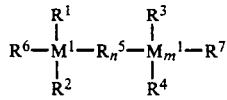  (I)

in which $M^1$ is silicon or germanium,
m denotes zero or 1, n=zero when m=zero and n=zero or 1 when m=1,
$R^1$, $R^2$, $R^3$ and $R^4$ are identical or different and denote a hydrogen atom, a $C_1$–$C_{30}$-alkyl group, a $C_2$–$C_{10}$-alkenyl group, a $C_6$–$C_{10}$-aryl group, a $C_7$–$C_{40}$-arylalkyl group, a $C_7$–$C_{40}$-alkylaryl group, a $C_8$–$C_{40}$-arylalkenyl group, a $C_1$–$C_{10}$-alkoxy group, a $C_6$–$C_{10}$-aryloxy group, a halogenated $C_1$–$C_{20}$-alkyl group, a halogenated $C_6$–$C_{10}$-aryl group or a halogen atom, or $R^1$ and $R^2$ or $R^3$ and $R^4$, together with the atom connecting them, form a ring,
$R^5$ denotes a $C_1$–$C_8$-alkylene group, a $C_6$–$C_{10}$-arylene group, a $C_7$–$C_{40}$-arylalkylene group, a $C_7$–$C_{40}$-alkylarylene group, an —O[Si(CH$_3$)$_2$—O]$_p$—group in which p is an integer from 1 to 5, or a chalcogen atom, and
$R^6$ and $R^7$ are identical or different and denote an unsubstituted or substituted indenyl radical, with the exception of 1,1'-(dimethylsilanediyl)bisindenyl.

The invention furthermore relates to a process for the preparation of this compound.

In the formula I, $M^1$ is silicon or germanium. m is zero or 1. When m=zero, n is likewise zero and when m=1, n is zero or 1.

$R^1$, $R^2$, $R^3$ and $R^4$ are identical or different and denote a hydrogen atom, a $C_1$–$C_{30}$-, preferably $C_1$–$C_2$-alkyl group, a $C_2$–$C_{10}$-, preferably $C_2$-alkenyl group, a $C_6$–$C_{10}$-, preferably $C_6$-aryl group, a $C_7$–$C_{40}$-, preferably $C_7$-arylalkyl group, a $C_7$–$C_{40}$-, preferably $C_7$–$C_9$-alkylaryl group, a $C_8$–$C_{40}$-, preferably $C_8$-arylalkenyl group, a $C_1$–$C_{10}$-, preferably $C_1$–$C_3$-alkoxy group, a $C_6$–$C_{10}$-, preferably $C_6$-aryloxy group, a halogenated $C_1$–$C_{20}$-, preferably $C_1$–$C_3$-alkyl group, in particular perfluoroalkyl group, a halogenated $C_6$–$C_{10}$-, preferably $C_6$-aryl group, in particular a perfluoroaryl group, or a halogen atom, preferably chlorine.

$R^1$ and $R^2$ or $R^3$ and $R^4$ can also form a ring together with the atom connecting them, preferably a 4–6-atom ring.

In particular, $R^1$, $R^2$, $R^3$ and $R^4$ denote methyl, ethyl, phenyl or vinyl.

$R^5$ is a $C_1$–$C_8$-, preferably $C_2$-alkylene group, a $C_6$–$C_{10}$-, preferably $C_6$-arylene group, a $C_7$–$C_{40}$-, preferably $C_7$–$C_9$-arylalkylene group, a $C_7$–$C_{40}$-, preferably $C_7$–$C_9$-alkylarylene group, a —O[Si(CH$_3$)$_2$—O]$_p$—group where p is an integer from 1 to 5, or a chalcogen atom, preferably oxygen.

$R^6$ and $R^7$ are identical or different, preferably identical, and denote an unsubstituted or substituted indenyl group. Examples of substituted indenes are: 1-(trimethylsilyl)indene, 1-phenylindene, 1-, 2-, 4- or 5-methoxyindene, 1-, 2-, 4- or 5-methylindene and 4-, 5-, 5- or 7-fluoroindene. Indene or 1-methylindene is preferably employed.

The bisindenyl derivative of the formula I according to the invention is prepared by reacting a compound of the formula II

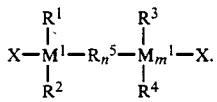  (II)

in which $M^1$, $R^1$, $R^2$, $R^3$, $R^4$, m and n have the abovementioned meaning and X is a halogen atom, preferably chlorine, with a compound of the formula III or IV

  (III),

  (IV)

in which $R^6$ and $R^7$ have the abovementioned meaning and $M^2$ is an alkali metal atom, preferably potassium or lithium, in particular lithium.

The reaction is carried out in an inert solvent which has been rendered absolute. Suitable solvents are aromatic hydrocarbons, such as, for example, toluene or xylene, aliphatic hydrocarbons, such as, for example, hexane or pentane, or ethers, such as, for example, diethyl ether, tetrahydrofuran and dioxane. Diethyl ether is preferably used.

The reaction temperature is −40° to 100° C., preferably 0° C. to 50° C.

The reaction time is 1 to 100 hours, preferably 4 to 20 hours, of which ¼ to 20 hours, preferably 1 to 4 hours, are used for the addition of the solution of compound III to the solution or the suspension of compound II. In all cases, compound III or IV is added to compound II.

The reaction is carried out with stirring and in an inert gas atmosphere. The process according to the invention has the advantage over the synthetic methods known that the silyl- or germyl-bridged bisindenyl compounds are produced in significantly higher yields due to inversion of the sequence of addition.

All the working operations below have been carried out in an inert gas atmosphere using solvents which have been rendered absolute (Schlenk technique).

EXAMPLE 1

1,1'-(dimethylsilanediyl)bisindenyl (1)

80 cm$^3$ (0.20 mol) of a 2.5 molar solution of n-butyllithium in hexane were added with ice cooling to a solution of 30 g (0.23 mol) of indene (technical grade, ≈91%), which has been filtered through aluminum oxide, in a 200 cm$^3$ of diethyl ether. The batch was stirred for a further 15 minutes at room temperature, and the orange solution was added through a canular over the course of 2 hours to a solution of 13.0 g (0.10 mol) of dimethyldichlorosilane (99%) in 30 cm$^3$ of diethyl ether. The orange suspension was stirred overnight and extracted by shaking three times with 100–150 cm$^3$ of water. The yellow organic phase was dried twice over sodium sulfate and evaporated in a rotary evaporator. The orange oil which remained was kept at 40° C. in an oil-pump vacuum for 4 to 5 hours and freed from excess indene, whereupon a white precipitate was deposited. It was possible to isolate a total of 20.4 g (71%) of compound 1 as a white to beige powder by adding 40 cm$^3$ of methanol and crystallizing at −35° C. m.p. 79°–81° C.

$^1$H NMR spectrum (CDCl$_3$): 2 diastereomers (≈1:1), 7.14–7.50 (arom. H), 6.40–6.90 (olefinic H), 3.62 (allylic H), −0.47, −0.28, −0.06 ppm (SiCH$_3$). Correct elemental analysis.

EXAMPLE 2

The procedure was analogous to Example 1. After the indene had been stripped off in an oil-pump vacuum, the crude product was chromatographed on 350 g of silica gel 60. It was possible to elute 23.6 g (82%) of compound 1 using hexane/methylene chloride (5:1 parts by volume).

EXAMPLE 3

7.8 g (0.20 mol) of potassium cut into small pieces were introduced into 100 cm$^3$ of tetrahydrofuran. 30 cm$^3$ (0.23 mol) of indene (technical grade ≈91%) which had been filtered through aluminum oxide were added dropwise over the course of 1 hour with vigorous stirring at a rate such that the solvent boiled gently. The batch was subsequently refluxed for a further 2 hours until the potassium had reacted completely. The indenylpotassium solution prepared in this way was reacted analogously to Example 1 with dimethyldichlorosilane and worked up. 16.1 g (56%) of compound 1 were obtained as a white powder.

EXAMPLE 4

1,1'-(diethylsilanediyl)bisindenyl 2

A solution of 15.7 g (0.10 mol) of diethyldichlorosilane in 30 cm$^3$ of diethyl ether was reacted analogously to Example 1 with 0.20 mol of indenyllithium solution and worked up. The oil remaining after stripping-off in an oil-pump vacuum was chromatographed on 400 g of silica gel 60. The product was eluted in a pale yellow zone using hexane/methylene chloride (10:1 parts by volume). After the solvent had been stripped off and the product had been recrystallized from hexane at −35° C., 19.5 g (62%) of compound 2 were obtained as a beige powder.

$^1$H NMR spectrum (CDCl$_3$): 2 diastereomers (≈1:1), 7.1–7.6 (arom. H), 6.2–7.0 (olefinic H), 3.6 (allylic H), 0.1–0.8 ppm (SiC$_2$H$_5$). Correct elemental analyses.

EXAMPLE 5

1,1'-(methylphenylsilanediyl)bisindenyl (3)

A solution of 19.1 g (0.10 mol) of methylphenyldichlorosilane (98%) in 30 cm$^3$ of diethyl ether was reacted analogously to Example 1 with 0.20 mol of lithiumindenyl solution and worked up. A total of 30.1 g (86%) of compound 3 (white crystalline powder) crystallized from hexane at −35° C.

$^1$H NMR spectrum (CDCl$_3$): 3 diastereomers (11:2:1), 7.0–7.5 (arom. H), 6.5–6.9 olefinic H), 3.91–3.97 (allylic H), −0.31, −0.14, −0.03 ppm (SiCH$_3$). Correct elemental analyses.

EXAMPLE 6

1,1'-diphenylsilanediyl)bisindenyl (4)

A solution of 25.3 g (0.10 mol) of diphenyldichlorosilane (99%) in 40 cm$^3$ of diethyl ether was reacted analogously to Example 1 with 0.20 mol of lithiumindenyl solution and worked up. The brown oil remaining after stripping-off in an oil-pump vacuum was chromatographed on 350 g of silica gel 60. Using hexane/toluene (3:1 parts by volume), it was possible to elute a total of 16.0 g (39%) of compound 4 which were produced as a base powder after the solvent had been stripped off.

$^1$H NMR spectrum (CDCl$_3$): 2 diastereomers (≈1:1), 7.0–7.5 (arom. H), 6.05–6.95 (olefinic H), 4.28, 4.33 ppm (allylic H). Correct elemental analyses.

The mass spectrum exhibited the decomposition pattern to be expected.

EXAMPLE 7

1,1'-(phenylvinylsilanediyl)bisindenyl (5)

A solution of 20.3 g (0.10 mol) of phenylvinyldichlorosilane in 30 cm$^3$ of diethyl ether was reacted analogously to Example 1 with 0.20 mol of lithiumindenyl solution and worked up. 16.3 g (45%) of compound 5 were precipitated from hexane at −35° C. as a white powder.

$^1$H NMR spectrum (CDCl$_3$) 2 diastereomers (4:1), 7.0–7.6 (arom. H), 6.5–6.9 (olefinic H), 5.32–6.15 (vinylic H), 4.02, 4.06 ppm (allylic H). Correct elemental analyses.

EXAMPLE 8

1,1'-(methylvinylsilanediyl)bisindenyl (6)

14.1 g (0.10 mol) of methylvinyldichlorosilane in 30 cm$^3$ of diethylether were reacted analogously to Example 1 with 0.20 mol of lithiumindenyl solution and worked up. A total of 14.4 g (48%) of compound 6 crystallized from hexane at −35° C.

$^1$H NMR spectrum (CDCl$_3$): 7.1–7.5 (m, 8, arom. H), 6.92–6.96 (m, 2, β-olefinic H), 6.63 (dd, 1, α-olefinic H), 6.57 (dd, 1 α-olefinic H), 5.42–5.90 (m, 3, vinylic H), 3.66 (s, 2, allylic H), −0.25 ppm (s, 3, SiCH$_3$). Correct elemental analyses.

EXAMPLE 9

1,1'-(phenylsilanediyl)bisindenyl (7)

17.7 g (0.10 mol) of phenyldichlorosilane in 30 cm$^3$ of diethyl ether were reacted analogously to Example 1 with 0.20 mol of lithiumindenyl solution and worked up. The oil remaining after stripping-off in an oil-pump vacuum was filtered through a frit with 15 cm of silica gel 60 using hexane/toluene (2:1 parts by volume). Hexane was added to the oil remaining after the solvent had been stripped off. 24.2 g (72%) of compound 7 crystalized out at −35° C.

$^1$H NMR spectrum (CDCl$_3$): 3 diastereomers, 7.0–7.5 (arom. H), 6.4–6.9 (olefinic H), 4.42, 4.27, 3.85 (3× t, Si—L H), 4.00, 3.87, 3.85, 3.60 ppm (4×m, allylic H). The mass and infra-red spectra corresponded to expectations. Correct elemental analyses.

EXAMPLE 10

1,1'-[1,2-ethanediylbis(dimethylsilyl)]bisindenyl (8)

A solution of 21.5 g (0.10 mol) of 1,2-bis-(chlorodimethylsilyl)ethane (80%) in 50 cm$^3$ of diethylether was reacted analogously to Example 1 with 0.20 mol of lithiumindenyl solution and worked up. 28.2 g (82%) of compound 8 crystallized out in the form of colorless crystals from hexane at −35° C. m.p. 71°–74° C.

$^1$H NMR spectrum (CDCl$_3$): 7.1–7.5 (arom. H), 6.90 (β-olefinic H), 6.57 (α-olefinic H), 3.53 (allylic H), 0.25–0.46 (C$_2$H$_4$), −0.10, −0.11, −0.15, −0.16 (SiCH$_3$). Correct elemental analyses.

EXAMPLE 11

1,1'-[bis(dimethylsilyl)]bisindenyl (9)

An ethereal solution of 0.30 mol of indenyllithium was added dropwise at 0° C. over the course of one hour to a solution of 26.0 g (0.14 mol) of tetramethyldichlorosilane in 250 cm$^3$ of diethyl ether. After the mixture had been stirred at room temperature for 1 hour, 50 cm$^3$ of water were added, the organic phase was separated off and dried over magnesium sulfate, and the solvent was removed. The residue was washed with methanol and dried and in vacuo.

Yield: 26.5 g (55%).

$^1$H NMR spectrum (CDCl$_3$): 2 diastereomers (=1:1), 7.45–7.11 (m, 8, arom. H), 6.86, 6.84 (2×ddd, 2 olefinic H), 6.59, 6.46 (2×dd, 2 olefinic H), 3.43, 3.32 (2×m, 2 allylic H), 0.05, −0.04, −0.16 m −0.31 (4×s, 4×3H, Si—CH$_3$).

EXAMPLE 12

1,1'-(dimethylsilanediyl)bis(3-methylindenyl) (10)

45 cm$^3$ (0.18 mol) of a 2.5 molar solution of n-butyllithium in n-hexane were added at 0° C. to a solution of 24.7 g (0.19 mol) of 1-methylindene in 200 cm$^3$ of diethyl ether. After the mixture had been stirred at room temperature for 20 minutes, the yellow solution was added through a canular over the course of 2 hours to a solution of 12.3 g (0.09 mol) of dimethyldichlorosilane in 30 cm$^3$ of diethyl ether, and the batch were stirred overnight. Work-up was analogous to Example 1. 20.4 g (68%) of compound 10 crystallized out in the form of yellow crystals from hexane at −35° C.

$^1$H NMR spectrum (CDCl$_3$): 2 diastereomers (≈1:1), 7.1–7.5 (arom. H), 6.26, 6.13 (α-olefinic H), 3.48 (allylic H), 2.22 (indene-CH$_3$), −0.15, −0.31, −0.48 (SiCH$_3$). Correct elemental analyses.

EXAMPLE 13

1,1'-(dimethylgermanediyl)bisindenyl (11)

A solution of 5.0 g (0.028 mol) of dimethyldichlorogermane in a 10 cm$^3$ of diethyl ether was reacted analogously to Example 1 with 0.058 mol of indenyllithium solution and worked up. Crystallization from n-hexane at −35° C. gave 7.2 g (75%) of compound 11 as a white powder.

$^1$H NMR spectrum (CDCl$_3$): 2 diastereomers (≈1:1), 7.1–7.5 (arom. H), 6.9–7.1 (β-olefinic H), 6.42–6.65 (α-olefinic H), 3.77 (allylic H) 0.09, −0.13, −0.30 ppm (GeCH$_3$). Correct elemental analyses.

EXAMPLE 14

1,1'-(diethylgermanediyl)bisindenyl (12)

A solution of 25 g (0.125 mol) of diethyldichlorogermane in 30 cm$^3$ of diethyl ether was reacted analogously to Example 1 at room temperature with 0.25 mol of indenyllithium solution and worked up. The oil remaining after stripping-off in an oil-pump vacuum was chromatographed on 350 g of silica gel 80. Compound 12 was eluted using hexane/methylene chloride (20:1 parts by volume) and subsequently recrystallized from a little hexane at −35° C. Yield: 27.9 g (62%) of white powder.

$^1$NMR spectrum (CDCl$_3$): 2 diastereomers (1:1), 7.0–7.6 (arom. H), 6.32–6.62 (olefinic H), 3.75 (allylic H), 0.35–0.87 (GeC$_2$H$_5$). Correct elemental analyses.

We claim:

1. A bisindenyl derivative of the formula I

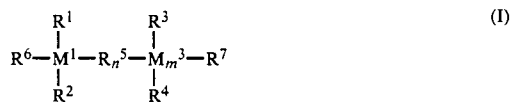

in which M$^1$ and M$^3$ are silicon or germanium wherein M$^1$ and M$^3$ can be identical or different, m is zero or 1, n=zero when m=zero and n=zero or 1 when m=1, R$^1$, R$^2$, R$^3$ and R$^4$ are identical or different and denote a hydrogen atom, a C$_1$–C$_{30}$-alkyl group, a C$_2$–C$_{10}$-alkenyl group, a C$_6$–C$_{10}$-aryl group, a C$_7$–C$_{40}$-arylalkyl group, a C$_7$–C$_{40}$-alkylaryl group, a C$_8$–C$_{40}$-arylalkenyl group, a C$_1$–C$_{10}$-alkoxy group, a C$_6$–C$_{10}$-aryloxy group, a halogenated C$_1$–C$_{20}$-alkyl group a halogenated C$_6$–C$_{10}$-aryl group or a halogen atom, or R$^1$, R$^2$, R$^3$ and R$^4$, together with the atom connecting them, form a ring, R$^5$ denotes a C$_1$–C$_8$-alkylene group, a C$_6$–C$_{10}$-arylene group, a C$_7$–C$_{40}$-arylalkylene group, a C$_7$–C$_{40}$-alkylarylene group, an —O[Si(CH$_3$)$_2$—O]$_p$—group in which p denotes an integer from 1 to 5, or a chalcogen atom, and R$^6$ and R$^7$ are identical or different and denote an, unsubstituted or substituted indenyl radical, with the exception of 1,1'-(dimethylsilanediyl)-bisindenyl.

2. A process for the preparation of a bisindenyl derivative of the formula I

in which M$^1$ and M$^3$ are silicon or germanium wherein M$^1$ and M$^3$ can be identical or different, m is zero or 1, n=zero when m=zero and n=zero or 1 when m=1, $R^1$, $R^2$, $R^3$ and $R^4$ are identical or different and denote a hydrogen atom, a $C_1$-$C_{30}$-alkyl group, a $C_2$-$C_{10}$-alkenyl group, a $C_6$-$C_{10}$-aryl group, a $C_7$-$C_{40}$-arylalkyl group, a $C_7$-$C_{40}$-alkylaryl group, a $C_8$-$C_{40}$-arylalkenyl group, a $C_1$-$C_{10}$-alkoxy group, a $C_6$-$C_{10}$-aryloxy group, a halogenated $C_1$-$C_{20}$-alkyl group, a halogenated $C_6$-$C_{10}$-aryl group or a halogen atom, or $R^1$, $R^2$, $R^3$ and $R^4$, together with the atom connecting them, form a ring, $R^5$ denotes a $C_1$-$C_8$-alkylene group, a $C_6$-$C_{10}$-arylene group, a $C_7$-$C_{40}$-aralkylene group, a $C_7$-$C_{40}$-alkylarylene group, an —O[Si(CH$_3$)$_2$—O]$_p$—group in which p denotes an integer from 1 to 5, or a chalcogen atom, and $R^6$ and $R^7$ are identical or different and denote an unsubstituted or substituted indenyl radical, by reacting an indenyl (alkali metal) compound with a dichlorosilyl compound, which comprises introducing a compound of the formula II

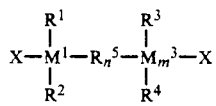  (II)

in which $M^1$, $M^3$, $R^1$, $R^2$, $R^3$, $R^4$, m and n have the abovementioned meanings and X is a halogen atom, in solution or suspension and adding the solution of the compound of the formula III or IV $R^6$-$M^2$   (III), $R^7$-$M^2$   (IV), in which $R^6$ and $R^7$ have the abovementioned meaning and $M^2$ is an alkali metal atom, at a temperature of from $-40°$ to $100°$ C. over the course of 1 to 100 hours to the solution or suspension of compound II.

3. The bisindenyl derivative of claim 1, wherein said $R^1$, $R^2$, $R^3$, and $R^4$ denote a $C_1$-$C_2$-alkyl group, a $C_2$-alkenyl group, a $C_6$-aryl group, a $C_7$-aryl alkyl, a $C_7$-$C_9$-alkyl aryl group, a $C_8$-arylalkenyl group, a $C_1$-$C_3$-alkoxy group, a $C_6$-aryloxy group, a halogenated $C_1$-$C_3$-alkyl group, a perfluoroalkyl group, a halogenated $C_6$-aryl group, a perfluoroaryl group, or a chlorine.

4. The bisindenyl derivative of claim 1, wherein said $R^1$, $R^2$, $R^3$, and $R^4$ form a 4–6 atom ring.

5. The bisindenyl derivative of claim 1, wherein $R^1$, $R^2$, $R^3$, and $R^4$ denote methyl, ethyl, phenyl, or vinyl.

6. The bisindenyl derivative of claim 1 wherein $R^5$ is a $C_2$-alkylene group, a $C_6$-arylene group, a $C_7$-$C_9$-aryl alkylene group, a $C_7$-$C_9$-alkylarylene group, or oxygen.

7. The bisindenyl derivative of claim 1, wherein said $R^6$ and $R^7$ are identical and are indene or 1-methylidene.

8. The process of claim 2, wherein X is chlorine.

9. The process of claim 2, wherein $M^2$ is potassium or lithium.

10. The process of claim 2, wherein said reaction temperature ranges from $0°$ C. to $50°$ C.

11. The process of claim 2, wherein said reaction time ranges from 4 to 20 hours.

12. A process for the preparation of a bisindenyl derivative of the formula I

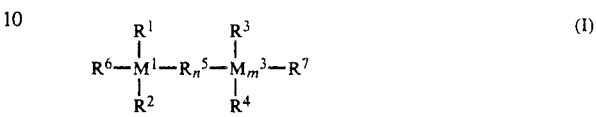  (I)

in which $M^1$ and $M^3$ are silicon or germanium wherein $M^1$ and $M^3$ can be identical or different, m is zero or 1, n=zero when m=zero and n=zero or 1 when m=1, $R^1$, $R^2$, $R^3$ and $R^4$ are identical or different and denote a hydrogen atom, a $C_1$-$C_{30}$-alkyl group, a $C_2$-$C_{10}$-alkenyl group, a $C_6$-$C_{10}$-aryl group, a $C_7$-$C_{40}$-arylalkyl group, a $C_7$-$C_{40}$-alkylaryl group, a $C_8$-$C_{40}$-arylalkenyl group, a $C_1$-$C_{10}$-alkoxy group, a $C_6$-$C_{10}$-aryloxy group, a halogenated $C_1$-$C_{20}$-alkyl group, a halogenated $C_6$-$C_{10}$-aryl group or a halogen atom, or $R^1$, $R^2$, $R^3$ and $R^4$, together with the atom connecting them, form a ring, $R^5$ denotes a $C_1$-$C_8$-alkylene group, a $C_6$-$C_{10}$-arylene group, a $C_7$-$C_{40}$-arylalkylene group, a $C_7$-$C_{40}$-alkylarylene group, an —O[Si(CH$_3$)$_2$—O]$_p$—group in which p denotes an integer from 1 to 5, or a chalcogen atom, and $R^6$ and $R^7$ are identical or different and denote an unsubstituted or substituted indenyl radical, by reacting an indenyl (alkali metal) compound with a compound of formula III or IV, which comprises introducing a compound of the formula II

  (II)

in which $M^1$, $M^3$, $R^1$, $R^2$, $R^3$, $R^4$, m and n have the abovementioned meanings and X is a halogen atom, in solution or suspension and adding the solution of the compound of the formula III or IV $R^6$-$M^2$   (III), $R^7$-$M^2$   (IV), in which $R^6$ and $R^7$ have the abovementioned meaning and $M^2$ is an alkali metal atom, at a temperature of from $-40°$ to $100°$ C. over the course of 1 to 100 hours to the solution or suspension of compound II.

* * * * *